United States Patent
Yoon et al.

(10) Patent No.: US 9,823,566 B2
(45) Date of Patent: Nov. 21, 2017

(54) MONOMER, HARDMASK COMPOSITION COMPRISING MONOMER, AND PATTERN FORMING METHOD USING HARDMASK COMPOSITION

(71) Applicant: CHEIL INDUSTRIES INC., Gumi-si, Gyeongsangbuk-do (KR)

(72) Inventors: Yong-Woon Yoon, Suwon-si (KR); Sung-Jae Lee, Suwon-si (KR); Joon-Young Moon, Suwon-si (KR); You-Jung Park, Suwon-si (KR); Chul-Ho Lee, Suwon-si (KR); Youn-Jin Cho, Suwon-si (KR)

(73) Assignee: CHEIL INDUSTRIES, INC., Gumi-Si, Gyeongsangbuk-Do (KR)

( * ) Notice: Subject to any disclaimer, the term of this patent is extended or adjusted under 35 U.S.C. 154(b) by 0 days.

(21) Appl. No.: 14/764,869

(22) PCT Filed: May 8, 2013

(86) PCT No.: PCT/KR2013/003993
§ 371 (c)(1),
(2) Date: Jul. 30, 2015

(87) PCT Pub. No.: WO2014/129701
PCT Pub. Date: Aug. 28, 2014

(65) Prior Publication Data
US 2015/0362837 A1     Dec. 17, 2015

(30) Foreign Application Priority Data

Feb. 21, 2013  (KR) .......................... 10-2013-0018735

(51) Int. Cl.
| | |
|---|---|
| G03F 7/11 | (2006.01) |
| C07D 303/32 | (2006.01) |
| C09D 163/00 | (2006.01) |
| G03F 7/20 | (2006.01) |
| G03F 7/32 | (2006.01) |
| C07D 303/14 | (2006.01) |
| C09D 5/00 | (2006.01) |
| C09D 7/12 | (2006.01) |
| G03F 7/34 | (2006.01) |

(52) U.S. Cl.
CPC .............. G03F 7/11 (2013.01); C07D 303/14 (2013.01); C07D 303/32 (2013.01); C09D 5/00 (2013.01); C09D 7/1233 (2013.01); C09D 163/00 (2013.01); G03F 7/20 (2013.01); G03F 7/32 (2013.01); G03F 7/34 (2013.01)

(58) Field of Classification Search
CPC ...... C09D 163/00; C09D 7/1233; C09D 5/00; C07D 303/32; C07D 303/14; C07D 407/10; C08G 59/22; G03F 7/11; G03F 7/32; G03F 7/34; G03F 7/20; G03F 7/004; H01L 21/027; H01L 21/0274–21/0276; H01L 21/0272
See application file for complete search history.

(56) References Cited

U.S. PATENT DOCUMENTS

| | | | | |
|---|---|---|---|---|
| 5,302,672 A | * | 4/1994 | Ogura | .................. C07C 37/20 525/481 |
| 2006/0216519 A1 | * | 9/2006 | Kimura | ................ C08G 59/245 428/413 |

FOREIGN PATENT DOCUMENTS

| | | |
|---|---|---|
| CN | 1991581 A | 7/2007 |
| CN | 101238414 A | 8/2008 |
| CN | 101470352 A | 7/2009 |
| CN | 102574963 A | 7/2012 |
| JP | 07-145346 A * | 6/1995 |
| JP | 2011-139118 A | 7/2011 |
| JP | 2011-150023 A | 8/2011 |
| JP | 2012-203393 A | 10/2012 |
| KR | 10-0663818 B1 | 1/2007 |
| KR | 10-0725794 B1 | 5/2007 |
| KR | 10-2011-0040666 A | 4/2011 |
| KR | 10-2011-0139118 A | 12/2011 |
| KR | 10-2012-0067602 A | 6/2012 |
| KR | 10-2012-0068379 A | 6/2012 |
| KR | 10-2012-0088669 A | 8/2012 |
| KR | 10-1216402 B1 | 12/2012 |
| KR | 10-2014-0083621 A | 7/2014 |
| TW | 201144375 A1 | 12/2011 |

(Continued)

OTHER PUBLICATIONS

Naito et al , "Negative-type chemically amplified resists for ArF excimer laser lithography", Proc. SPIE vol. 3333, Advances in Resist Technology and Processing XV, pp. 503-511 (Jun. 29, 1998); doi: 10.1117/12.312364.*

(Continued)

*Primary Examiner* — Cynthia Hamilton
(74) *Attorney, Agent, or Firm* — Lee & Morse, P.C.

(57) ABSTRACT

Disclosed are a monomer for a hardmask composition represented by the following Chemical Formula 1, a hardmask composition including the monomer, and a method of forming patterns using the hardmask composition.

[Chemical Formula 1]

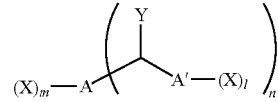

In the above Chemical Formula 1,
A, A', X, Y, I, m and n are the same as described in the detailed description.

20 Claims, No Drawings

(56) References Cited

FOREIGN PATENT DOCUMENTS

TW           201217430 A1    5/2012
WO   WO 2010/055852 A1    5/2010

OTHER PUBLICATIONS

English translation of JP 07-145346 A 9 published Jun. 1995, obtained from AIPN Japan Patent Office National Center for Industrial Property Information and Training, generated Jan. 20, 2016, 7 pages.*
Search Report dated Jan. 27, 2015 in corresponding Taiwanese Patent Application No. 102125735.

* cited by examiner

MONOMER, HARDMASK COMPOSITION COMPRISING MONOMER, AND PATTERN FORMING METHOD USING HARDMASK COMPOSITION

TECHNICAL FIELD

A monomer, a hardmask composition including the monomer, and a method of forming a pattern using the hardmask composition are disclosed.

BACKGROUND ART

Recently, the semiconductor industry has developed to an ultra-fine technique having a pattern of several to several tens nanometer size. Such ultrafine technique essentially needs effective lithographic techniques.

The typical lithographic technique includes providing a material layer on a semiconductor substrate; coating a photoresist layer thereon; exposing and developing the same to provide a photoresist pattern; and etching the material layer using the photoresist pattern as a mask.

Nowadays, according to small-sizing the pattern to be formed, it is difficult to provide a fine pattern having an excellent profile by only above-mentioned typical lithographic technique. Accordingly, a layer, called a hardmask layer, may be formed between the material layer and the photoresist layer to provide a fine pattern.

The hardmask layer plays a role of an intermediate layer for transferring the fine pattern of photoresist to the material layer through the selective etching process. Accordingly, the hardmask layer is required to have characteristics such as heat resistance and etch resistance, and the like to be tolerated during the multiple etching processes.

DISCLOSURE

Technical Problem One embodiment provides monomer for a hardmask composition that may reduce out-gas generation due to excellent cross-linking.

Another embodiment provides a hardmask composition including the monomer.

Yet another embodiment provides a method of forming patterns using the hardmask composition.

Technical Solution

According to one embodiment, a monomer for a hardmask composition represented by the following Chemical Formula 1 is provided:

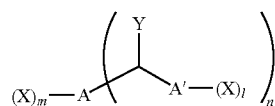

[Chemical Formula 1]

In the above Chemical Formula 1,

A is a substituted or unsubstituted polycyclic aromatic group, A' is a substituted or unsubstituted C6 to C20 arylene group, X is an epoxy group, Y is hydrogen, a hydroxy group, a C1 to C10 alkylamine group, an amino group ($-NH_2$), =O, or a combination thereof, l is an integer of 0 to 6, and m and n are independently integers of 1 to 4.

The A may be a substituted or unsubstituted polycyclic aromatic group selected from the following Group 1.

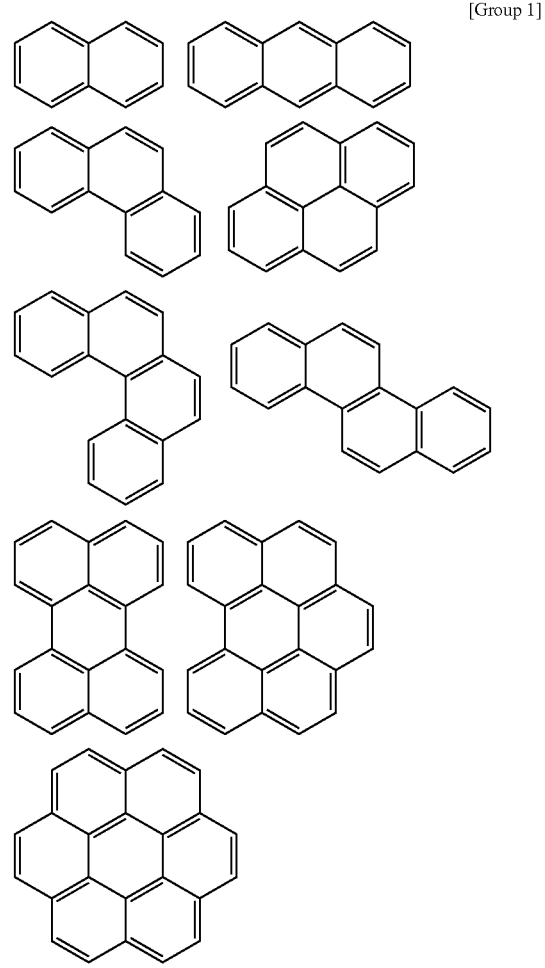

[Group 1]

The A' may be a C6 to C20 arylene group substituted with a hydroxy group, a thionyl group, a thiol group, a cyano group, a substituted or unsubstituted amino group, a substituted or unsubstituted C1 to 010 alkylamine group, or a combination thereof.

The monomer may be represented by one of the following Chemical Formulae 2 to 5.

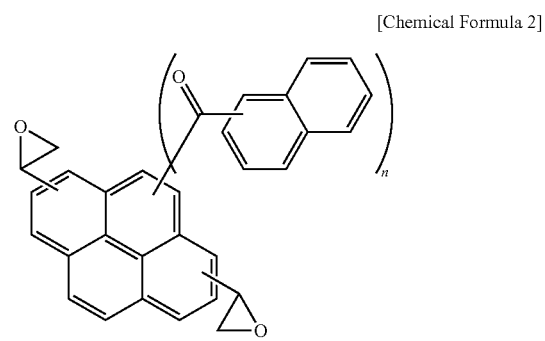

[Chemical Formula 2]

-continued

[Chemical Formula 3]

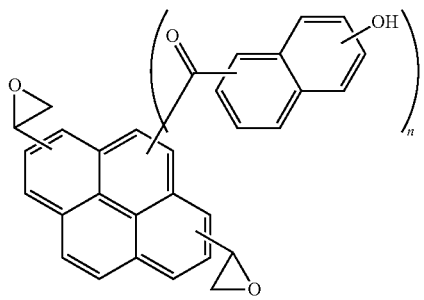

[Chemical Formula 4]

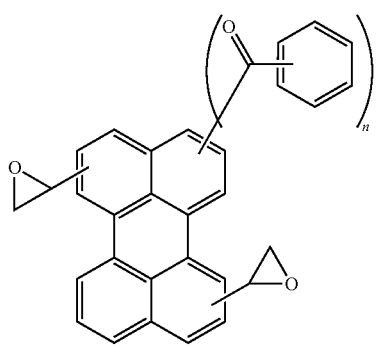

[Chemical Formula 5]

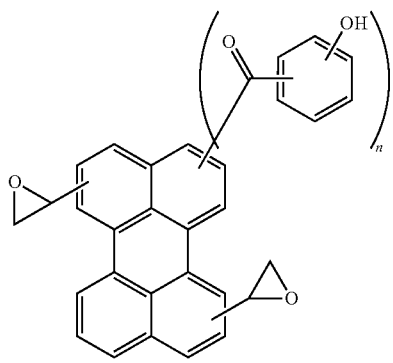

In the above Chemical Formulae 2 to 5, n is independently an integer of 1 to 4.

The monomer may have a molecular weight of 200 to 5,000.

According to another embodiment, a hardmask composition including the monomer and a solvent is provided.

The monomer may be included in an amount of 0.1 to 50 wt % based on the total amount of the hardmask composition.

According to yet another embodiment, a method of forming patterns includes providing a material layer on a substrate, applying the hardmask composition on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The hardmask composition may be applied using a spin-on coating method.

Technical Solution

The hardmask layer may be formed by heat-treating at 100° C. to 500° C.

The hardmask composition has reduced out-gas generation due to excellent cross-linking and simultaneously improves etch resistance.

Best Mode

Hereinafter, exemplary embodiments of the present invention will hereinafter be described in detail so that a person skilled in the art would understand. However, this disclosure may, however, be embodied in many different forms and is not construed as limited to the exemplary embodiments set forth herein.

In this specification, when a definition is not otherwise provided, 'substituted' refers to one substituted with at least a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocycloalkyl group, and a combination thereof, instead of hydrogen of a compound.

In this specification, when a definition is not otherwise provided, 'hetero' refers to one including 1 to 3 heteroatoms selected from N, O, S and P.

Hereinafter, a monomer for a hardmask composition according to one embodiment is described.

A monomer for a hardmask composition according to one embodiment may be represented by the following Chemical Formula 1.

[Chemical Formula 1]

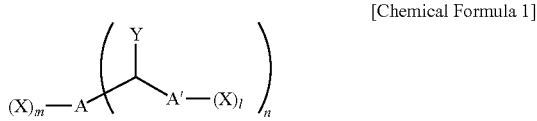

In the above Chemical Formula 1,

A is a substituted or unsubstituted polycyclic aromatic group, A' is a substituted or unsubstituted C6 to C20 arylene group, X is an epoxy group, Y is hydrogen, a hydroxy group, a C1 to C10 alkylamine group, an amino group (—NH$_2$), =O, or a combination thereof, l is an integer of 0 to 6, and m and n are independently integers of 1 to 4.

The monomer includes a polycyclic aromatic group in a core, and an epoxy group linked to the polycyclic aromatic group.

The monomer has a polycyclic aromatic group and thus, may secure a rigid characteristic.

The epoxy group may increase cross-linking capability of the monomer during the curing and thus, a cross-linking density. Accordingly, the hardmask composition is cured at a relatively low temperature and may form a thin film having excellent chemical resistance and etch resistance and high uniformity. The number of the epoxy group linked to the polycyclic aromatic group is in a range of 1 to 4, for example, greater than or equal to 2.

On the other hand, a substituent linked to the core includes a C6 to C20 arylene group, and the number of carbon in the arylene group may be changed to adjust properties of the monomer.

The monomer may include an epoxy group in the substituent as well as in the core.

The A may be a substituted or unsubstituted polycyclic aromatic group selected from the following Group 1.

[Group 1]

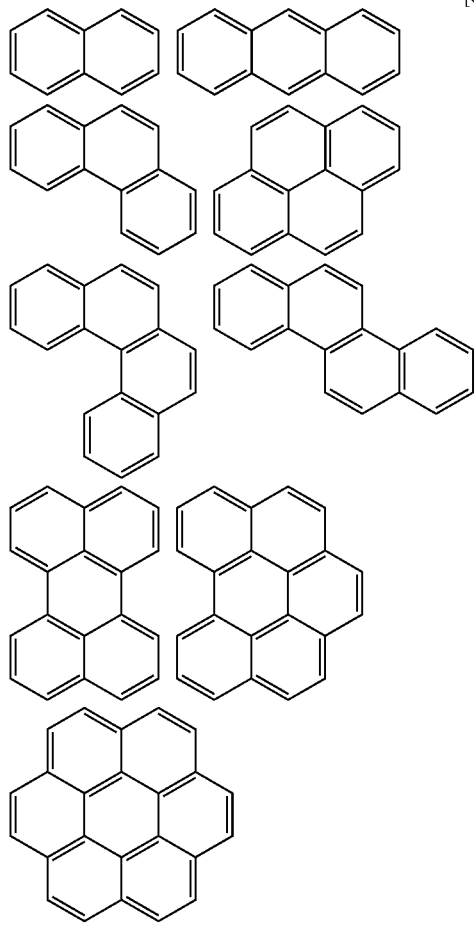

In the Group 1, each ring may be substituted or unsubstituted without a particular limit to its linking position. The rings arranged in the Group 1 are substituted with, for example, a C1 to C20 alkyl group, a halogen atom, a hydroxy group, and the like, but the substituent has no particular limit.

The C6 to C20 arylene group may be substituted with at least one of a hydroxy group, a thionyl group, a thiol group, a cyano group, a substituted or unsubstituted amino group, a substituted or unsubstituted C1 to C10 alkylamine group, or a combination thereof, which may perform amplified cross-linkings due to a condensation reaction with a functional group represented by Y in the above Chemical Formula 1.

The monomer may be represented by one of the following Chemical Formulae 2 to 5.

[Chemical Formula 2]

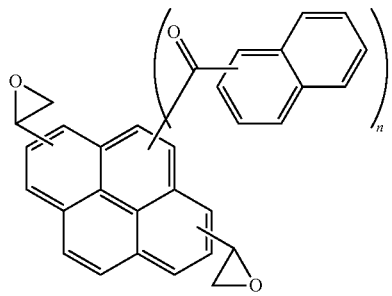

[Chemical Formula 3]

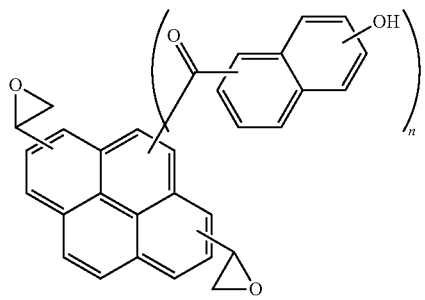

[Chemical Formula 4]

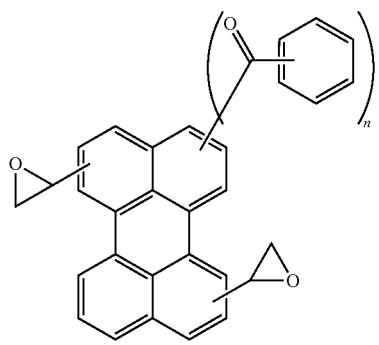

[Chemical Formula 5]

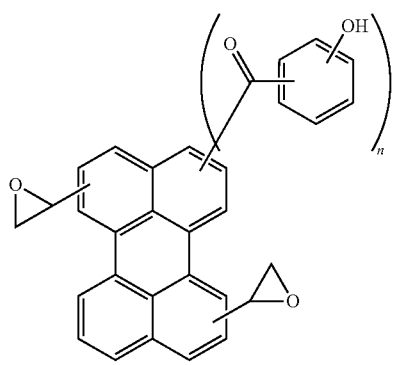

In the above Chemical Formulae 2 to 5, n is independently an integer of 1 to 4.

The monomer may have a molecular weight of 200 to 5000, for example 300 to 2,000. When the monomer has a molecular weight within the above range, solubility of the monomer having a high carbon content for a solvent is improved and an improved thin layer may be obtained through spin-on coating.

Hereinafter, a hardmask composition according to one embodiment is described.

The hardmask composition according to one embodiment includes the above monomer and a solvent.

The monomer is the same as described above, and one kind of monomer may be included singularly or two or more kinds of monomer may be mixed.

The solvent may be any solvent having sufficient dissolution or dispersion for the monomer without limitation, and may be for example at least one selected from propylene glycol, propylene glycol diacetate, methoxy propane diol, diethylene glycol, diethylene glycol butylether, tri(ethylene glycol)monomethylether, propylene glycol monomethylether, propylene glycol monomethylether acetate, cyclohexanone, ethyl lactate, gamma-butyrolactone, methyl pyrrolidone, acetylacetone, and ethyl 3-ethoxy propionate.

The monomer may be included in an amount of 0.1 to 50 wt % based on the total amount of the hardmask composition. When the monomer is included in the above range, a thickness of a coated thin film may be obtained.

The hardmask composition may further include a surfactant.

The surfactant may include, for example, alkylbenzene sulfonate salt, alkyl pyridinium salt, polyethylene glycol, or a quaternary ammonium salt, but is not limited thereto.

The surfactant may be included in an amount of 0.001 to 3 parts by weight based on 100 parts by weight of the hardmask composition. Within the above range, the solubility and the cross-linking may be secured while not changing the optical properties of the hardmask composition.

Hereafter, a method for forming patterns by using the hardmask composition is described.

A method of forming patterns according to one embodiment includes providing a material layer on a substrate, applying the hardmask composition including the monomer and solvent, on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer and etching an exposed part of the material layer.

The substrate may be, for example, a silicon wafer, a glass substrate, or a polymer substrate.

The material layer is a material to be finally patterned, for example a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The hardmask composition may be applied by spin-on coating in a form of a solution. Herein, the hardmask composition may be applied at a thickness, for example 50 Å to 50,000 Å.

The heat-treating the hardmask composition may be performed, for example 100 to 500° C. for 10 seconds to 10 minutes. During heat-treating, the monomer may cause a self cross-linking and/or mutual cross-linking reaction.

The silicon-containing thin layer may be made of, for example silicon nitride or silicon oxide.

A bottom antireflective coating (BARC) may be further formed on the silicon-containing thin layer.

Exposure of the photoresist layer may be performed using, for example ArF, KrF, or EUV. After exposure, heat treatment may be performed at 100° C. to 500° C.

The etching process of the exposed part of the material layer may be performed through a dry etching process using an etching gas and the etching gas may be, for example $CHF_3$, $CF_4$, $Cl_2$, $BCl_3$, and a mixed gas thereof.

The etched material layer may be formed in a plurality of pattern, and the plurality of pattern may be a metal pattern, a semiconductor pattern, an insulation pattern, and the like, for example diverse patterns of a semiconductor integrated circuit device.

Mode for Invention

Hereinafter, the present disclosure is illustrated in more detail with reference to examples. However, these examples are exemplary, and the present disclosure is not limited thereto.

Synthesis of Monomer

Synthesis Example 1

2.86 g (0.01 mol) of 2,7-di(oxiran-2-yl)pyrene and 5.72 g (0.03 mol) of 2-naphthoyl chloride, and 50 ml of dichloroethane were put in a 100 ml flask under a nitrogen atmosphere and agitated for 1 hour, and 2.93 g (0.022 mol) of $AlCl_3$ was slowly added thereto. The mixture was agitated at room temperature. Then, 50 ml of deionized water was added, completing the reaction (12 hr, RT) after confirming if the starting materials were all removed through gel permeation chromatography (GPC). 50 ml of ethyl acetate was used to extract an organic layer, and the organic layer was twice rinsed with 30 ml of deionized water and concentrated under a reduced pressure, obtaining a compound represented by the following Chemical Formula 6.

[Chemical Formula 6]

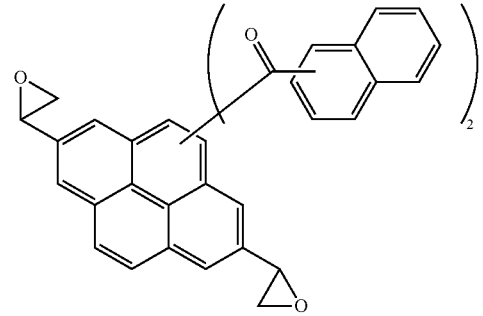

The yield of the compound was 81%, and the compound had an average molecular weight of 510.

Synthesis Example 2

3.36 g (0.01 mol) of 2,7-di(oxiran-2-yl)pyrene, 4.68 g (0.03 mol) of 4-hydroxy benzoyl chloride, and 50 ml of dichloroethane were put in a 100 ml flask and agitated for 1 hour, and 4.39 g (0.033 mol) of $AlCl_3$ was slowly added thereto. The mixture was agitated at room temperature. 50 ml of deionized water was added to the resultant, completing the reaction (18 hr, RT) after confirming if the starting materials were all removed through gel permeation chromatography (GPC). 50 ml of ethyl acetate was used to extract an organic layer, and the organic layer were twice rinsed with 30 ml of deionized water and concentrated under a reduced pressure, obtaining a compound represented by the following Chemical Formula 7.

[Chemical Formula 7]

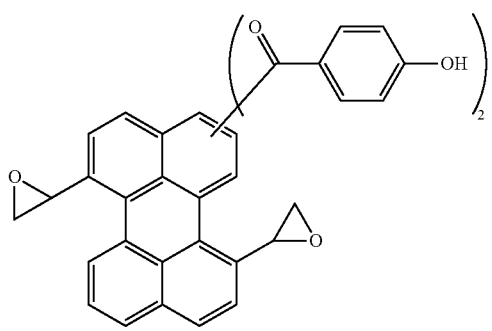

The yield of the compound was 72%, and the compound had an average molecular weight of 565.

Comparative Synthesis Example 1

A compound represented by the following Chemical Formula 8 was synthesized according to the same method as Synthesis Example 1 except for using pyrene as a starting material.

[Chemical Formula 8]

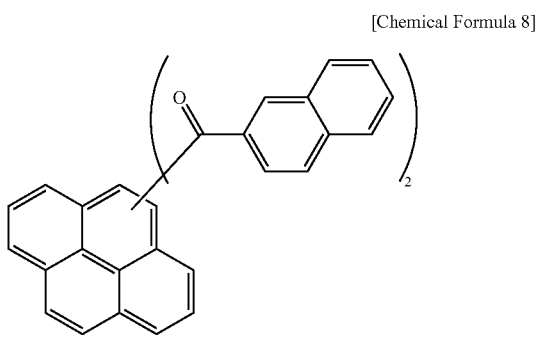

The yield of the compound was 68%, and the compound had an average molecular weight of 470.

Comparative Synthesis Example 2

A compound represented by the following Chemical Formula 9 was synthesized according to the same method as Synthesis Example 2 except for using perylene as a starting material.

[Chemical Formula 9]

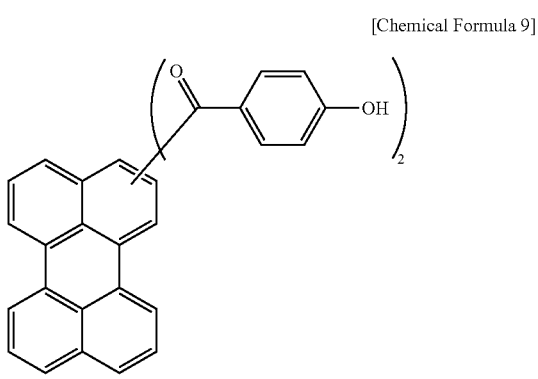

The yield of the compound was 79%, and the compound had an average molecular weight of 553.

Preparation of Hardmask Composition

Example 1

1 g of the compound according to Synthesis Example 1 was completely dissolved in 9 g of propylene glycol monomethyl ether acetate (PGMEA), preparing a hardmask composition.

Example 2

1 g of the compound according to Synthesis Example 2 was completely dissolved in 9 g of propylene glycol monomethyl ether acetate (PGMEA), preparing a hardmask composition.

Comparative Example 1

1g of the compound according to Comparative Synthesis Example 1 was completely dissolved in 9 g of propylene glycol monomethyl ether acetate (PGMEA), preparing a hardmask composition.

Comparative Example 2

1 g of the compound according to Comparative Synthesis Example 2 was completely dissolved in 9 g of propylene glycol monomethyl ether acetate (PGMEA), preparing a hardmask composition.

Evaluation

Evaluation 1: Out-Gas Evaluation

The hardmask compositions according to Examples 1 and 2 and Comparative Examples 1 and 2 were respectively spin-on coated on a silicon wafer, forming about 2,000 Å-thick thin films. The films were baked at 180° C. for 120 seconds, and out-gas produced during the baking was measured using QCM (Quartz Crystal Microbalance).

The out-gas evaluation results are provided in Table 1.

TABLE 1

| | Out-gas (ng/100 Å) |
|---|---|
| Example 1 | 1.7 |
| Example 2 | 1.6 |
| Comparative Example 1 | 2.4 |
| Comparative Example 2 | 2.1 |

Referring to Table 1, the hardmask compositions according to Examples 1 and 2 showed less amount of out-gas than the hardmask compositions according to Comparative Examples 1 and 2 at the same temperature of 180° C.

The reason is that the hardmask compositions according to Examples 1 and 2 had excellent cross-linking compared with the hardmask compositions according to Comparative Examples 1 and 2, and accordingly, the hardmask compositions according to Examples 1 and 2 might be stably baked.

Evaluation 2: Evaluation of Etching Resistance

The hardmask compositions according to Examples 1 and 2 and Comparative Examples 1 and 2 were spin-on coated on a silicon wafer and heat-treated on a hot plate at 240° C. and 400° C. for 120 seconds, forming each thin film. Then, thicknesses of the thin films were measured using a measuring device made by K-MAC.

The thin films were dry-etched for 60 seconds by using $N_2/O_2$ mixed gas, and the thicknesses of the thin films were measured. In addition, the thin films were dry-etched for 100 seconds by using $CF_x$ gas, and thicknesses of the thin films were measured.

The thicknesses of the thin films before and after the dry etching and etching time were used to calculate a bulk etch rate (BER) according to the following Calculation Equation 1.

[Calculation Equation 1]

(Initial thin film thickness—thin film thickness after etching)/etching time (Å/s)

The results are provided in Table 2.

TABLE 2

| | Etch rate(Å/s) | | | |
|---|---|---|---|---|
| | $N_2/O_2$ | | $CF_x$ | |
| | 240° C. | 400° C. | 240° C. | 400° C. |
| Example 1 | 22.08 | 18.71 | 24.54 | 26.17 |
| Example 2 | 21.24 | 17.36 | 23.22 | 26.20 |
| Comparative Example 1 | 24.72 | 22.35 | 27.07 | 30.33 |
| Comparative Example 2 | 23.57 | 22.21 | 26.94 | 29.12 |

Referring to Table 2, the thin films formed of the hardmask compositions according Examples 1 and 2 showed sufficient etching resistance for etching gas compared with the hardmask compositions according to Comparative Examples 1 and 2 and thus, a low etch rate.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A monomer for a hardmask composition, the monomer being represented by the following Chemical Formula 1:

[Chemical Formula 1]

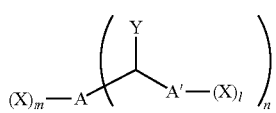

wherein, in the above Chemical Formula 1,
A is a substituted or unsubstituted polycyclic aromatic group,
A' is a substituted or unsubstituted C6 to C20 arylene group,
X is an epoxy-containing group,
Y is a hydroxy group, a C1 to C10 alkylamine group, —$NH_2$, =O, or a combination thereof,
l is an integer of 0 to 6, and
m and n are each independently an integer of 1 to 4.

2. The monomer of claim 1, wherein A is a substituted or unsubstituted one of the following polycyclic aromatic groups:

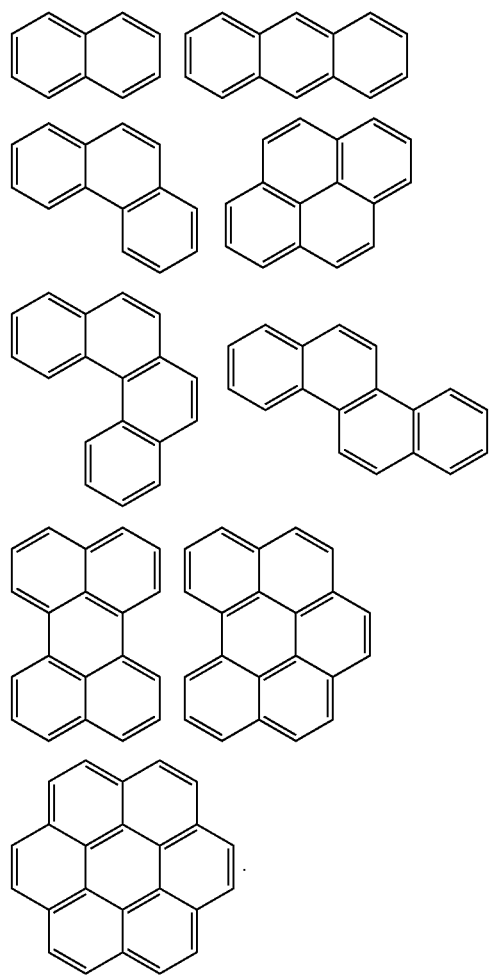

3. The monomer of claim 1, wherein A' is the substituted C6 to C20 arylene group, the substituted C6 to C20 arylene group being substituted with a hydroxy group, a thionyl group, a thiol group, a cyano group, a substituted or unsubstituted amino group, a substituted or unsubstituted C1 to C10 alkylamine group, or a combination thereof.

4. The monomer of claim 1, wherein the monomer is represented by one of the following Chemical Formulae 2 to 5:

[Chemical Formula 2]

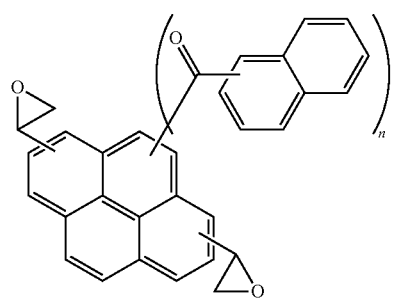

-continued

[Chemical Formula 3]

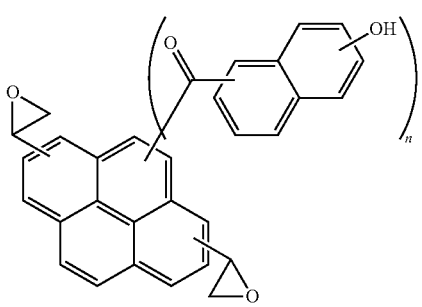

[Chemical Formula 4]

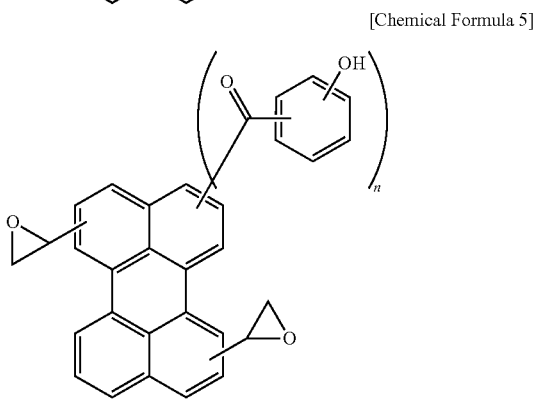

[Chemical Formula 5]

wherein, in the above Chemical Formulae 2 to 5, n is an integer of 1 to 4.

5. The monomer of claim 1, wherein the monomer has a molecular weight of 200 to 5,000.

6. A hard mask composition, comprising:
a monomer represented by the following Chemical Formula 1, and a solvent:

[Chemical Formula 1]

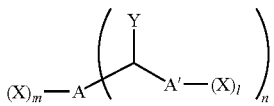

wherein, in the above Chemical Formula 1,
A is a substituted or unsubstituted polycyclic aromatic group,
A' is a substituted. or unsubstituted C6 to C20 arylene group,
X is an epoxy-containing group,
Y is a hydroxy group, a C1 to C10 alkylamine group, $-NH_2$, $=O$, or a combination thereof, l is an integer of 0 to 6, and
m and n are each independently an integer of 1 to 4.

7. The hardmask composition of claim 6, wherein A is a substituted or unsubstituted one of the following polycyclic aromatic groups.

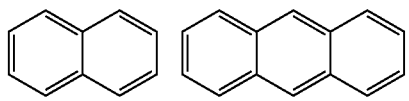

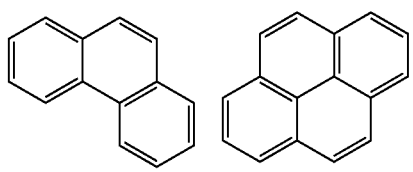

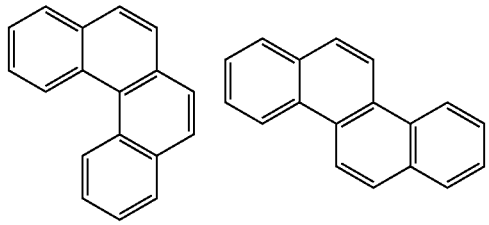

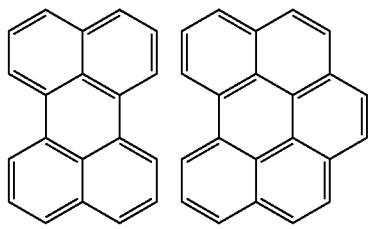

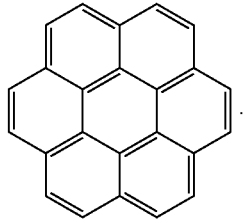

8. The hardmask composition of claim 6, wherein A' is the substituted C6 to C20 arylene group, the substituted C6 to C20 arylene group being substituted with a hydroxy group, a thionyl group, a thiol group, a cyano group, a substituted or unsubstituted amino group, a substituted or unsubstituted C1 to C10 alkylamine group, or a combination thereof.

9. The hardmask composition of claim 6, wherein the monomer is represented by one of the following Chemical Formulae 2 to 5:

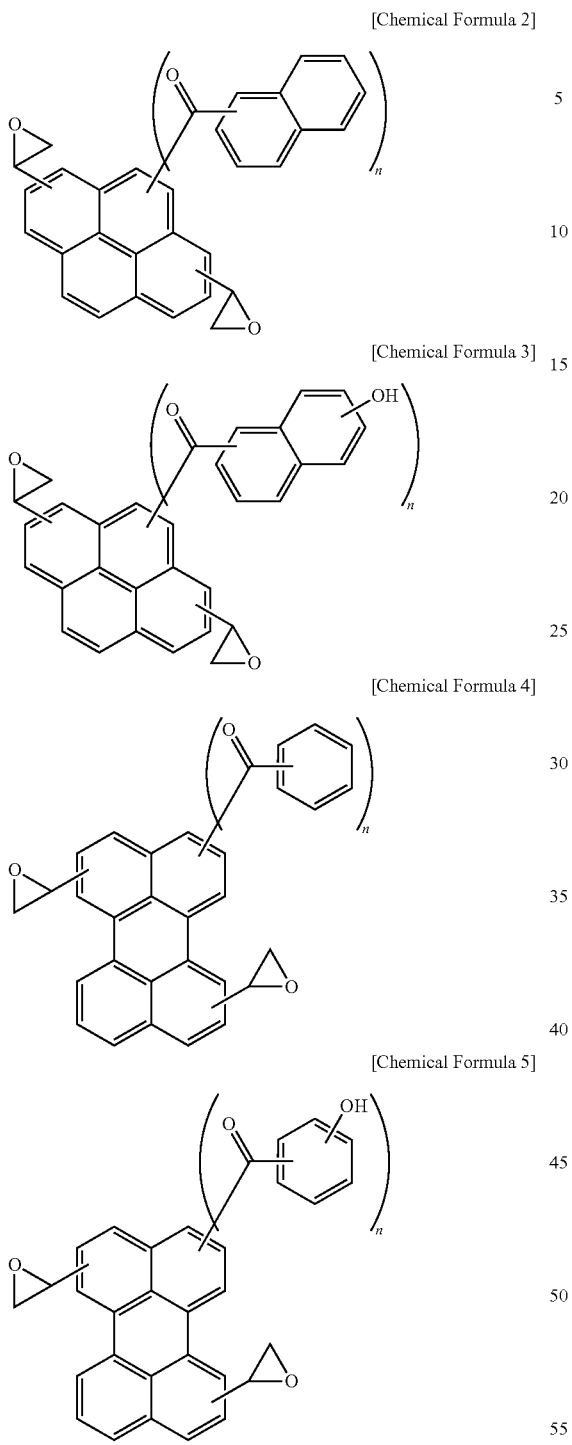

[Chemical Formula 2]

[Chemical Formula 3]

[Chemical Formula 4]

[Chemical Formula 5]

wherein, in the above Chemical Formulae 2 to 5, n is an integer of 1 to 4.

10. The hardmask composition of claim 6, wherein the monomer has a molecular weight of 200 to 5000.

11. The hardmask composition of claim 6, wherein the monomer is included in the composition in an amount of 0.1 to 50 wt %, based on a total weight of the hardmask composition.

12. A method of forming patterns, the method comprising:
providing a material layer on a substrate,
applying a hardmask composition on the material layer,
heat-treating the hardmask composition to form a hardmask layer,
forming a silicon-containing thin layer on the hardmask layer,
forming a photoresist layer on the silicon-containing thin layer,
exposing and developing the photoresist layer to form a photoresist pattern
selectively removing the silicon-containing thin layer and the hardmask layer using the photoresist pattern to expose a part of the material layer, and
etching an exposed part of the material layer,
wherein the hardmask composition includes;
a monomer represented by the following Chemical Formula 1, and a solvent:

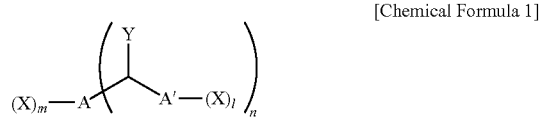

[Chemical Formula 1]

wherein, in the above Chemical Formula 1,
A is a substituted or unsubstituted polycyclic aromatic group,
A' is a substituted. or unsubstituted C6 to C20 arylene group,
X is an epoxy-containing group,
Y is hydrogen, a hydroxy group, a C1 to C10 alkylamine group, $-NH_2$, $=O$, or a combination thereof,
l is an integer of 0 to 6, and
m and n are each independently an integer of 1 to 4.

13. The method of claim 12, wherein applying the hardmask composition includes performing a spin-on coating method.

14. The method of claim 12, wherein heat-treating the hardmask layer is performed at 100° C. to 500° C.

15. The method of claim 12, wherein A is a substituted or unsubstituted one of the following polycyclic aromatic groups:

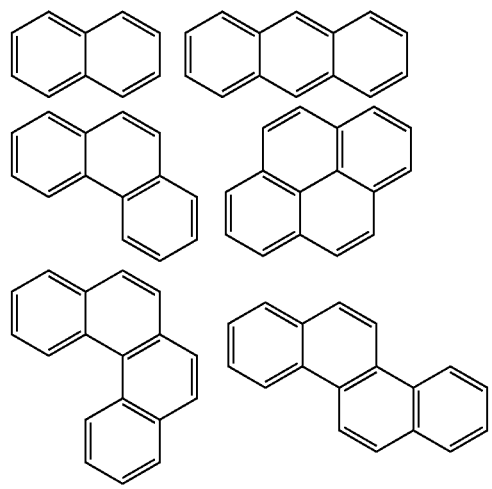

-continued

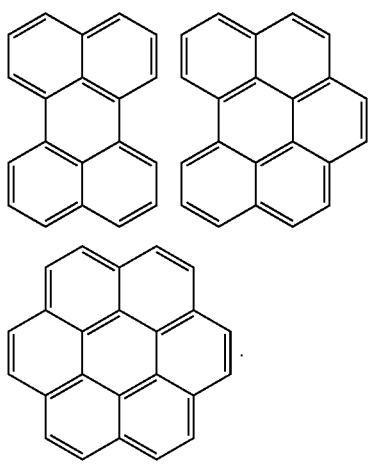

16. The method of claim 12, wherein A' is the substituted C6 to C20 arylene group, the substituted C6 to C20 arylene group being substituted with a hydroxy group, a thionyl group, a thiol group, a cyano group, a substituted or unsubstituted amino group, a substituted or unsubstituted C1 to C10 alkylamine group, or a combination thereof.

17. The method of claim 12, wherein the monomer is represented by one of the following Chemical Formulae 2 to 5:

[Chemical Formula 2]

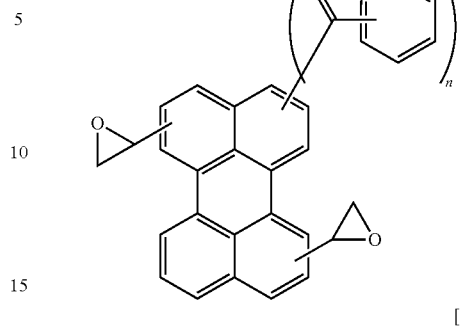

[Chemical Formula 3]

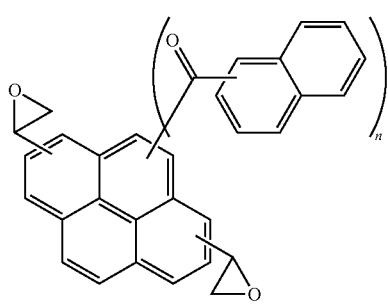

-continued

[Chemical Formula 4]

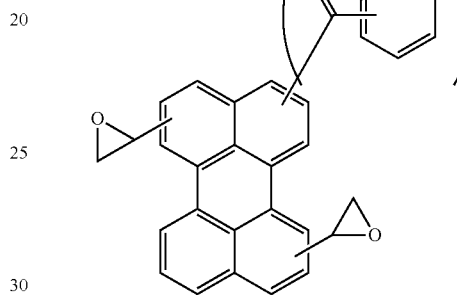

[Chemical Formula 5]

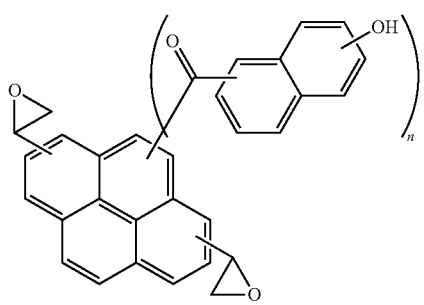

wherein, in the above Chemical Formulae 2 to 5, n is an integer of 1 to 4.

18. The method of claim 12, wherein the monomer has a molecular weight of 200 to 5000.

19. The method of claim 12, wherein the monomer is included in the composition in an amount of 0.1 to 50 wt %, based on a total weight of the hardmask composition.

20. A monomer for a hardmask composition, the monomer being represented by the following Chemical Formula 1:

[Chemical Formula 1]

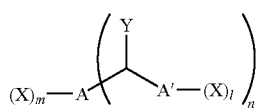

wherein, in the above Chemical Formula 1,
A is a substituted or unsubstituted polycyclic aromatic group,
A' is a substituted C6 to C20 arylene group, the substituted C6 to C20 arylene group being substituted with a hydroxy group, a thionyl group, a thiol group, a cyano group, a substituted or unsubstituted amino group, a substituted or unsubstituted C1 to C10 alkylamine group, or a combination thereof,
X is an epoxy-containing group,
Y is a hydrogen, a hydroxy group, a C1 to C10 alkylamine group, NH2, =O, or a combination thereof,
l is an integer of 0 to 6, and
m and n are each independently an integer of 1 to 4.

* * * * *